(12) United States Patent
Pasetti et al.

(10) Patent No.: US 6,350,437 B1
(45) Date of Patent: Feb. 26, 2002

(54) TOOTH PASTES

(75) Inventors: Marco Pasetti, Milan; Roberto Cerini, Padua, both of (IT)

(73) Assignee: Farmaceutici Dott. Ciccarelli S.p.A., Milan (IT)

( * ) Notice: Subject to any disclaimer, the term of this patent is extended or adjusted under 35 U.S.C. 154(b) by 0 days.

(21) Appl. No.: 09/523,727

(22) Filed: Mar. 13, 2000

(30) Foreign Application Priority Data

Mar. 12, 1999 (IT) .......................................... MI99A0502

(51) Int. Cl.⁷ .............................. A61K 7/16; A61K 7/20; A61K 7/48; A61K 47/45
(52) U.S. Cl. ............................................ 424/53; 424/49
(58) Field of Search ....................................... 424/49–58

(56) References Cited

FOREIGN PATENT DOCUMENTS

| EP | 0 325 288 B1 | 7/1989 |
|----|--------------|--------|
| EP | 0 325 289 B1 | 7/1989 |
| EP | 0 424 020 A1 | 4/1991 |
| EP | 0 545 594 A1 | 6/1993 |
| EP | 0 852 259 A1 | 8/1998 |
| EP | 0 895 777 A2 | 2/1999 |
| WO | WO 96/05802  | 2/1996 |

*Primary Examiner*—Shep K. Rose
(74) *Attorney, Agent, or Firm*—Arent, Fox, Kintner, Plotkin & Kahn

(57) ABSTRACT

Tooth pastes comprising:
a) imido-alkanpercarboxylic acids under the form of adducts with cyclodextrins, preferably beta-cyclodextrins,
b) aliphatic carboxylic acids having a solubility in water at room temperature higher than or equal to 5% by weight and containing one or more carboxylic functions.

19 Claims, No Drawings

TOOTH PASTES

The present invention relates to bleaching and hygienizing compositions having improved chemical and chemical-physical stability which is maintained during the time even after prolonged storage (shelf stability), even over 6 months.

More specifically the invention relates to compositions to be used for preparing tooth pastes of complex compositions.

The bleaching and hygienizing properties of organic peroxiacids, in particular of aliphatic peroxyphthalimidic acids, such as typically the epsilon-phthalimido peroxyhexanoic acid, known as PAP, are known, see for examples EP 325,289 and EP 325,288. The reactivity of the aliphatic peroxyphthalimidic acids makes their use interesting in various applications, but it is also a technical problem from the point of view of the preparation of formulations having high stability during the time. Indeed said organic peroxyacids react very quickly wherefore it is not possible to prepare complex formulations, such as those of the tooth pastes, stable during the time.

The shelf-stability of the tooth paste formulation is therefore an essential feature for the same.

In tooth pastes one could think to use organic peroxyacids and specifically the phthalimido-peroxyalkanoic acids introduced in many component compositions as chemical agents having bleaching and hygienizing action to improve these properties with respect to the conventional compositions, which are based on the physical-mechanical action of the abrasive compounds contained in the tooth pastes. However it must be noted that organic peroxides must be able to operate under particularly mild conditions and at the same time to maintain their activity during the time even after prolonged storage, without changing the system organoleptic characteristics, as defined below.

As regards tooth pastes it is known the efficacy of the proxyacetic acid for the preparation of formulations having an improved bleaching effect, see for example EP 545,594.

The efficacy of phthalimido-alkanoic and/or cationic peroxyacids for the preparation of tooth systems having a bleaching activity is also known, see for example patent application WO 96/05802. In the case of the phthalimido-peroxyalkanoic acids, which have a remarkable chemical reactivity and bleaching and hygienizing activity, besides favourable toxicological properties, it is difficult to obtain monocomponent formulations for tooth pastes having polyfunctional characteristics. In said patent application, in order to prepare tooth pastes, a bicomponent system formed of two complementary but separated formulations, which are mixed together at the time of the use, is employed. This solution allows to maintain all the properties of the phthalimido-alkanoic peroxyacids but from the practical point of view it represents a limitation since it requires more complex equipments typical of bicomponent systems.

The solution which allows to obtain a monocomponent formulation comprising the phthalimido-alkanoic proxyacids has been described in EP 895,777. In this patent adducts between said peroxyacids and cyclodextrins are used, which allow to improve the stability of the peroxycarboxylic acids without reducing the activity and efficacy thereof.

Tests carried out by the Applicant have shown that with the formulations exemplified for tooth pastes in EP 895,777 tooth pastes having a greater stability in the time are obtained, however it is required that tooth pastes of industrial and commercial interest show a greater stability as regards organoleptic properties, also in the long term. More specifically the stability required to tooth pastes of industrial and commercial interest represents not only the substantial maintenance of the active oxygen titre, the sole characteristic of stability reported in EP 895,777, but also the maintenance of the organoleptic properties such as: colour, taste, homogeneity (uniformity) of the paste for a long time, combined with easiness to flow from the consumer tube and maintenance of this feature for a long period, and of the chemical-physical properties such as: pH, density and viscosity.

The need was felt to have available commercially usable tooth paste compositions having improved stability as above defined.

It has been surprisingly and unexpectedly found by the Applicant that it is possible to further improve said stability by the formulations described hereinafter:

An object of the present invention are tooth pastes comprising:

a) imido-alkanpercarboxylic acids of general formula:

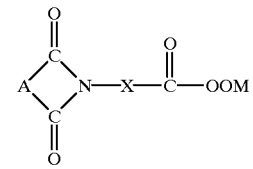

wherein A is a group of formula

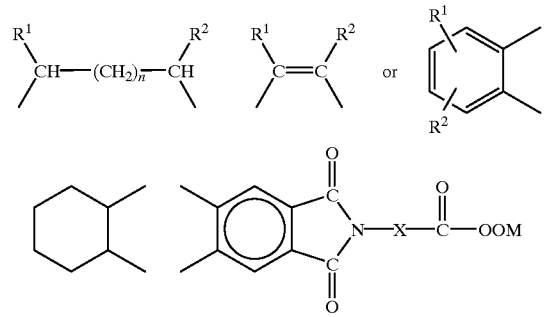

n is an integer 0, 1 or 2,
R$^1$ is hydrogen, chlorine, bromine, C$_1$–C$_{20}$ alkyl, C$_2$–C$_{20}$ alkenyl, aryl or alkylaryl,
R$^2$ is hydrogen, chlorine, bromine or a group of formula —SO$_3$M, —CO$_2$M, —CO$_3$M, —OSO$_3$M,
M is hydrogen, an alkaline metal or ammonium ion or the equivalent of an alkaline-earth metal ion and x is C$_1$–C$_{19}$ alkylene or arylene;
Y is a C$_3$–C$_{19}$, alkylene, under the form of adducts with cyclodextrins, preferably beta-cyclodextrins,
b) aliphatic carboxylic acids having a solubility in water at room temperature higher than or equal to 5% by weight and containing one or more carboxylic functions.

Aliphatic oxyacids containing one or more —OH functions are the preferred components b). In particular, as an example, lactic acid, citric acid, tartaric acid, etc., can be mentioned. Also various kinds of isomers can be used where possible. For example as for tartaric acid the (L), (D), meso or racemic form can be used.

The component b) amount ranges from 0.05 to 5% by weight, preferably 0.1–1% by weight, of the tooth paste.

Preferably component b) is used encapsulated, f.i. as it is common in the pharmaceutical field.

In component a) the molar ratio between the peroxyacids of the invention and cyclodextrins, PAP-cyclodextrins adduct, is in the range 1:1–1:2.

Among immidoalkanpercarboxylic acids of component a) the phthalimido-peroxycarboxylic acids are preferred, more preferably the epsilon-phthalimido-peroxyhexanoic acid.

Among cyclodextrins we can mention alpha, beta, gamma or delta cyclodextrins, modified alpha, beta, gamma or delta cyclodextrins with acyl, alkyl, hydroxyalkyl groups, generally having from 1 to 10 carbon atoms, preferably from 2 to 6; the mixtures of said cyclodextrins and the mixtures of said cyclodextrins with dextrins or linear oligosaccharides; beta-cyclodextrins are preferably used.

A process for preparing the adducts of peroxyacid and in particular of the epsilon-phthalimido peroxyhexanoic acid with cyclodextrins, in particular beta-cyclodextrins, is described in EP 895,777, herein incorporated by reference.

Tooth pastes contain as well known, among others, the conventional components indicated below, which must however show the characteristic to be chemically compatible with component a). This compatibility (COMPATIBILITY TEST) is experimentally determined by measurements of the adduct thermal stability in the presence of the single conventional component. By thermal stability it is meant the maintenance from the component a) of its titre in active oxygen, i.e. a maximum reduction of said titre of 10% after one week of exposure at the temperature of 450° C. As typical conventional components: wetting agents, preservatives, thickeners, dyes, aromas, sweeteners, abrasives and detergents can be mentioned.

It has been found by the Applicant that the above test is satisfied with the typical conventional components of the tooth paste.

Among wetting agents there can be water, glycerine, sorbitol; among preservatives: parabens, imidazolidinylurea; among thickeners: cellulose esters, alginates, silica, carrageen; among dyes those of common food use; among aromas especially the derivatives of mint, carnation, anise, orange, bergamot, eucalyptus, etc.; among sweeteners saccharin and its derivatives, xylitol and mannitol; among abrasives: silica, alumina, dihydrate calcium phosphate; among detergents sodium lauryl sulphate, etc.

Preferred tooth pastes according to the invention are the following: (% by weight):

| | | |
|---|---|---|
| sorbitol, glycerine | 40.0–55.0% | (wetting agents) |
| silica | 18.0–24.0% | (thickener/abrasive) |
| sodium laurylsulphate | 1.1–1.8% | (detergent) |
| carboxymethylcellulose | 0.8–1.5% | (thickener) |
| aroma | 0.7–1.5% | |
| sweetener (xylitol) | 0.1–10.0% | |
| sodium fluoride | 0.28–0.34% | |
| PAP-cyclodextrin adduct | 4.0–8.0% | |
| polysorbate 60 | 1.5–4.0% | (wetting agent) |
| encapsulated citric acid | 0.2–0.8% | |
| imidazolidinylurea | 0.1–0.15% | (preservative) |
| Jojoba esters and dye | 0.2–0.6% | |
| water | as suff. to 100% | (wetting agent) |

Aromas can be used as such, preferably they are used comilled. With comilled it is meant a mixture between aroma and an inert specific support, for example silica, carboxymethylcellulose and other cellulose derivatives, obtainable for example by a comilling process.

Some examples are hereinafter reported for illustrative purposes but they are not limitative of the present invention.

EXAMPLE 1

10 kg of tooth paste have been prepared with a turbo emulsifier under vacuum by using the following composition (in % by weight):

| | |
|---|---|
| sorbitol | 55.0% |
| silica | 19.0% |
| sodium laurylsulphate | 1.6% |
| carboxymethylcellulose | 1.2% |
| aroma | 1.0% |
| sweetener (saccarin) | 0.3% |
| sodium fluoride | 0.32% |
| PAP-cyclodextrin adduct | 5.0% |
| polysorbate 60 | 3.0% |
| encapsulated citric acid | 0.5% |
| imidazolidinylurea | 0.15% |
| Jojoba esters (dye) | 0.4% |
| water | as suff. to 100% |

The compatibility of each component has been evaluated by using the compatibility test indicated in the description. This test was satisfied by each component.

An uniform (homogeneous) product having the following characteristics was obtained:

organoleptic properties: a homogeneous translucid gel appearance having a green-blue colour and a pleasant, fresh and persistent taste, consistency of isotropic fluid; pH=5.7 (in dispersion at 10% in water at 25° C.), density 1.334 Kg/l at 20° C., viscosity 304,000 centipoise at 20° C. measured by Brookfield viscometer. The tooth paste obtained was put into a conventional tube for tooth paste and showed an easiness to flow for 8 months, by opening and closing the tube three times a day. The tooth paste maintained the homogeneity for 8 months. The test was stopped at 8 months.

The organoleptic characteristics have been evaluated as follows:

Appearance: visually;

Colour: visually;

Taste: during the use;

Consistency: visually.

The results are reported in Table 1.

EXAMPLE 2

10 kg of tooth paste have been prepared with a turbo emulsifier under vacuum by using the following composition (in % by weight):

| | |
|---|---|
| sorbitol | 55.0% |
| silica | 19.0% |
| sodium laurylsulphate | 1.6% |
| carboxymethylcellulose | 1.2% |
| comilled aroma | 3.2% |
| sweeteners | 0.3% |
| sodium fluoride | 0.32% |
| PAP-cyclodextrin adduct | 5.0% |
| polysorbate 60 | 3.0% |
| encapsulated citric acid | 0.5% |
| imidazolidinylurea | 0.15% |
| Jojoba esters (dye) | 0.4% |
| silica microgranules | 1.0% |
| water | as suff. to 100% |

The used comilled aroma was a mixture between aroma and silica (as support).

An uniform product having the following characteristics was obtained:

organoleptic properties: a homogeneous translucid gel appearance having a green-blue colour and a pleasant, fresh and persistent taste, consistence of isotropic fluid; pH=5.6 (in dispersion at 10% in water at 250° C.), density 1.330 Kg/l at 20° C., viscosity 306,000 centipoise at 20° C. measured by Brookfield viscometer.
The results are reported in Table 1.

EXAMPLE 3

10 kg of tooth paste have been prepared with a turbo emulsifier under vacuum by using the following composition (in % by weight):

| | |
|---|---|
| sorbitol | 35.0% |
| glycerine | 20.0% |
| silica | 19.0% |
| sodium laurylsulphate | 1.6% |
| carboxymethylcellulose | 1.2% |
| comilled aroma | 3.2% |
| sweeteners | 0.3% |
| sodium fluoride | 0.32% |
| PAP-cyclodextrin adduct | 5.0% |
| polysorbate 60 | 3.0% |
| encapsulated citric acid | 0.5% |
| imidazolidinylurea | 0.15% |
| Jojoba esters (dye) | 0.4% |
| silica microgranules | 1.0% |
| water | as suff. to 100% |

The used comilled aroma was a mixture between aroma and carboxymethylcellulose (as support).

An uniform product having the following characteristics was obtained:

organoleptic properties: a homogeneous translucid gel appearance having a green-blue colour and a pleasant, fresh and persistent taste, consistency of isotropic fluid; pH=5.9 (in dispersion at 10% in water at 250° C.), density 1.332 Kg/l at 20° C., viscosity 308,000 centipoise at 20° C. measured by Brookfield viscometer.
The results are reported in Table 1.

EXAMPLE 4 (comparative)

10 kg of tooth paste have been prepared with a turbo emulsifier under vacuum by using the following composition (in % by weight):

| | |
|---|---|
| sorbitol | 55.0% |
| silica | 19.0% |
| sodium laurylsulphate | 1.6% |
| carboxymethylcellulose | 1.2% |
| aroma | 1.0% |
| sweeteners | 0.3% |
| sodium fluoride | 0.32% |
| PAP-cyclodextrin adduct | 5.0% |
| polysorbate 60 | 3.0% |
| imidazolidinylurea | 0.15% |
| Jojoba esters (dye) | 0.4% |
| silica microgranules | 1.0% |
| water | as suff. to 100% |

An uniform product having the following characteristics was obtained:

organoleptic properties: a homogeneous translucid gel appearance having a green-blue colour and a pleasant, fresh and persistent taste, consistency of isotropic fluid; pH=6.9 (in dispersion at 10% in water at 25° C.), density 1.330 Kg/l at 20° C., viscosity 300,000 centipoise at 20° C. measured by Brookfield viscosimeter.
The results are reported in Table 1.

EXAMPLE 5

A quick ageing test has been carried out under controlled conditions by putting the samples of the tooth pastes obtained in the Examples from 1 to 4 in a stove at a constant temperature of 40° C. for 180 days.

The data noticed at the end of the ageing test concerning the organoleptic and chemical-physical properties of the samples are reported in Table 1.

TABLE 1

| SAMPLES | EXAMPLE 1 | EXAMPLE 2 | EXAMPLE 3 | EXAMPLE 4 (comparative) |
|---|---|---|---|---|
| appearance | unchanged | unchanged | unchanged | unchanged |
| colour | unchanged | unchanged | unchanged | gold-yellow |
| taste | unchanged | unchanged | unchanged | unsuitable |
| consistency | unchanged | unchanged | unchanged | unhomogeneous |
| pH | unchanged | unchanged | unchanged | 6.2 |
| density | unchanged | unchanged | unchanged | unchanged |
| viscosity | unchanged | unchanged | unchanged | n.d. |

The data show that the invention pastes remain stable from the organoleptic point of view also after quick ageing of 180 days and therefore they are suitable to marketing. The pastes not according to the invention lose their organoleptic characteristics due to ageing and therefore they have no industrial interest.

EXAMPLE 6

Example 3 has been repeated, but using as aroma a combination of free aroma and comilled aroma in the following amounts: 0.5% by weight and 2.7% by weight respectively.

Both the obtained product and its stability characterization (see Example 5) are similar to those of Example 3.

EXAMPLE 7

10 kg of tooth paste have been prepared with a turbo emulsifier under vacuum by using the following composition (in % by weight):

| | |
|---|---|
| sorbitol | 45.0% |
| silica | 19.0% |
| sodium laurylsulphate | 1.6% |
| carboxymethylcellulose | 1.3% |

-continued

| | |
|---|---|
| aroma | 3.45% |
| sweetener (xylitol) | 10.0% |
| sodium fluoride | 0.32% |
| PAP-cyclodextrin adduct | 5.0% |
| polysorbate 60 | 3.0% |
| imidazolidinylurea | 0.15% |
| encapsulated citric acid | 0.5% |
| Jojoba esters (dye) | 0.2% |
| silica microgranules | 1.0% |
| titanium dioxide (dye) | 1.0% |
| water | as suff. to 100% |

An uniform product having the following characteristics was obtained:
organoleptic properties: appearance of a paste with green-blue coloured microgranules having a pleasant, fresh and persistent taste, consistency of isotropic fluid; pH=5.8 (in dispersion at 10% in water at 25° C.), density 1.336 Kg/l at 200° C., viscosity 308,000 centipoise at 20° C. measured by Brookfield viscometer.

The organoleptic characteristics have been evaluated as before, the results are similar to Ex. 1.

The easiness to flow has been evaluated as in Ex. 1 but for 1 year. The tooth paste passed this test and homogeneity was maintained.

What is claimed is:

1. Tooth pastes comprising:
a) imido-alkanpercarboxylic acids of general formula:

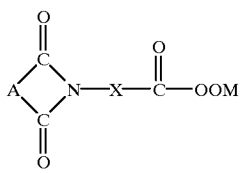

wherein A is a group of formula

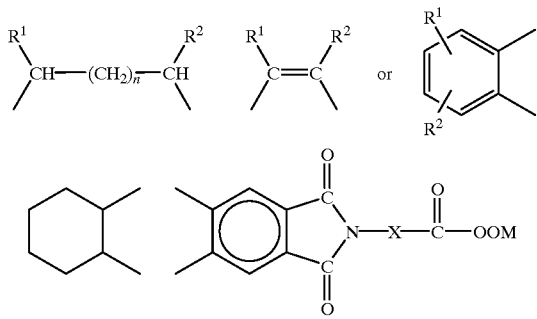

n is an integer 0, 1 or 2,
$R^1$ is hydrogen, chlorine, bromine, $C_1$–$C_{20}$ alkyl, $C_2$–$C_{20}$ alkenyl, aryl or alkylaryl,
$R^2$ is hydrogen, chlorine, bromine or a group of formula —$SO_3M$, —$CO_2M$, —$CO_3M$, —$OSO_3M$,
M is hydrogen, an alkaline metal or ammonium ion or the equivalent of an alkaline-earth metal ion and X is $C_1$–$C_{19}$ alkylene or arylene;
Y is a $C_3$–$C_{15}$ alkylene, under the form of adducts with cyclodextrins, admixed with
b) aliphatic carboxylic acids having a solubility in water at room temperature higher than or equal to 5% by weight and containing one or more carboxylic functions and a toothpaste oral carrier comprising conventional toothpaste components.

2. Tooth pastes according to claim 1, wherein the components b) are the aliphatic oxyacids containing one or more —OH functions, optionally mixed together.

3. Tooth pastes according to claim 2, wherein component b) is selected from one or more of the following: lactic acid, citric acid, tartaric acid.

4. Tooth pastes according to claim 1, wherein in component a) the molar ratio between peroxyacids and cyclodextrins is in the range 1:1–1:2.

5. Tooth pastes according to claim 4, wherein the adduct is PAP-cyclodextrins.

6. Tooth pastes according to claim 1, wherein the imidoalkanpercarboxylic acids of component a) are phthalimido-peroxycarboxylic acids.

7. Tooth pastes according to claim 6, wherein the phthalimi-do-pereoxycarboxylic acid is the epsilon-phthalimido-peroxyhexanoic acid.

8. Tooth pastes according to claim 1, wherein the cyclodextrins are alpha, beta, gamma or delta cyclodextrins optionally modified with acyl, alkyl, or hydroxyalkyl groups having from 1 to 10 carbon atoms, the mixtures of said cyclodextrins and dextrins or linear oligosaccharides.

9. Tooth pastes according to claim 1 wherein the conventional toothpaste components satisfy the following test: after exposure for one week at 45° C. of the adduct in the presence of a single conventional toothpaste component, the titre in active oxygen of the adduct is reduced no more than 10%.

10. Tooth pastes according to claim 9, wherein the conventional components are: wetting agents, preservatives, thickeners, dyes, aromas, sweeteners, abrasives and detergents.

11. Tooth pastes according to claim 10, wherein wetting agents are: water, glycerine, sorbitol; preservatives are: parabens, imidazolidinylurea; thickeners are: cellulose esters, alginates, silica, carrageen; dyes are those of common food use; aromas are the derivatives of mint, carnation, anise, orange, bergamot, eucalyptus; sweeteners are: saccharin and its derivatives, xylitol and mannitol; abrasives are: silica, alumina, dihydrate calcium phosphate; detergents are: sodium lauryl sulphate.

12. Tooth pastes according to claim 1, wherein the component b) amount ranges from 0.05 to 5% by weight, preferably 0.1–1% by weight, of the tooth paste.

13. Tooth pastes according to claim 1 having the following compositions (% by weight):

| | | |
|---|---|---|
| sorbitol, glycerine | 40.0–55.0% | (wetting agents) |
| silica (thickener/abrasive) | 18.0–24.0% | |
| sodium laurylsulphate | 1.1–1.8% | (detergent) |
| carboxymethylcellulose | 0.8–1.5% | (thickener) |
| aroma | 0.7–1.5% | |
| sweeteners | 0.1–10.0% | |
| sodium fluoride | 0.28–0.34% | |
| PAP-cyclodextrin adduct | 4.0–8.0% | |
| polysorbate 60 | 1.5–4.0% | (wetting agent) |
| encapsulated citric acid | 0.2–0.8% | |
| imidazolidinylurea | 0.1–0.15% | (preservative) |
| Jojoba esters and dye | 0.2–0.6% | |
| water | as suff. to 100% | (wetting agent) |

14. Tooth pastes according to claim 1, wherein the aromas are used as such, or comilled, or mixtures of the two, with comilled it is meant an inner mixture between aroma and an inert support.

15. Tooth pastes according to claim 14, wherein the support is silica, carboxymethylcellulose and other cellulose derivatives.

16. A process for the preparation of tooth pastes comprising admixing component a) with component b) and a toothpaste oral carrier comprising conventional toothpaste components, wherein component a) and b) are as follows:

a) imido-alkanpercarboxylic acids of general formula:

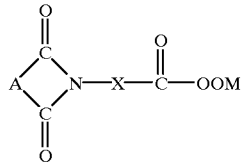

wherein A is a group of formula

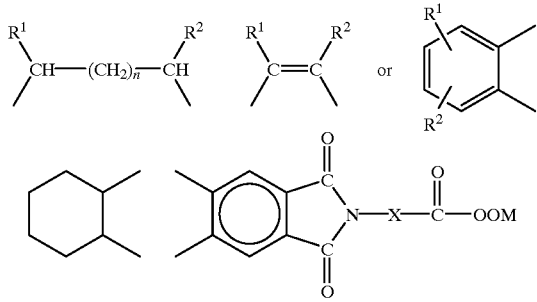

n is an integer 0, 1 or 2, $R^1$ is hydrogen, chlorine, bromine, $C_1$–$C_{20}$ alkyl, $C_2$–$C_{20}$ alkenyl, aryl or alkylaryl, $R^2$ is hydrogen, chlorine, bromine or a group of formula —$SO_3M$, —$CO_2M$, —$CO_3M$, —$OSO_3M$, M is hydrogen, an alkaline metal or ammonium ion or the equivalent of an alkaline-earth metal ion and X is $C_1$–$C_{19}$ alkylene or arylene;

Y is a $C_3$–$C_{15}$ alkylene, under the form of adducts with cyclodextrins, b) aliphatic carboxylic acids having a solubility in water at room temperature higher than or equal to 5% by weight and containing one or more carboxylic functions.

17. Tooth pastes according to claim 1 wherein Y is a $C_3$–$C_{15}$ alkylene, under the form of adducts with beta-cyclodextrins.

18. Tooth pastes according to claim 8, wherein the alpha, beta, gamma or delta cyclodextrins are optionally modified with acyl, alkyl or hydroxyalkyl groups having from 2 to 6 carbons.

19. Tooth pastes according to claim 18, wherein the cyclodextrins are beta-cyclodextrins.

* * * * *